United States Patent [19]
DeHaven-Hudkins et al.

[11] Patent Number: 5,240,935
[45] Date of Patent: Aug. 31, 1993

[54] SUBSTITUTED 2-AZABICYCLO[2.2.2]OCTANE DERIVATIVES AND COMPOSITIONS AND METHOD OF USE THEREOF

[75] Inventors: Diane L. DeHaven-Hudkins, Chester Springs, Pa.; John P. Mallamo, Kinderhook; William F. Michne, Poestenkill, both of N.Y.; Martha R. Heimann, Durham, N.C.

[73] Assignee: Sterling Winthrop Inc., New York, N.Y.

[21] Appl. No.: 979,040

[22] Filed: Nov. 20, 1992

[51] Int. Cl.$^5$ .................. A61K 31/435; C07D 221/22
[52] U.S. Cl. .................................... 514/295; 514/299; 546/93; 546/97; 546/112; 546/183
[58] Field of Search .................. 546/93, 97, 112, 183; 514/295, 299

[56] References Cited

U.S. PATENT DOCUMENTS

| | | | |
|---|---|---|---|
| 3,422,092 | 1/1969 | Moffett | 546/112 |
| 3,497,518 | 2/1970 | Moffett | 546/112 |
| 3,741,973 | 6/1973 | Fonken et al. | 546/112 |
| 3,780,022 | 12/1973 | Fonken et al. | 546/112 |
| 4,180,667 | 12/1979 | Michne | 546/112 |
| 4,563,464 | 1/1986 | Ezer et al. | 546/112 |
| 4,808,718 | 2/1989 | Hartman et al. | 546/112 |

OTHER PUBLICATIONS

Michne, J. Org. Chem. 1976, 41(5), 894–896.
Buchi, et al., J. Am. Chem. Soc. 1966, 88(13), 3099–3109.

*Primary Examiner*—Bernard Dentz
*Attorney, Agent, or Firm*—Michael D. Alexander; Paul E. Dupont

[57] ABSTRACT

Novel substituted 2-azabicyclo[2.2.2]octane derivatives, pharmaceutical compositions containing them, methods for treating central nervous system disorders utilizing them, and processes for synthesizing them.

19 Claims, No Drawings

SUBSTITUTED 2-AZABICYCLO[2.2.2]OCTANE DERIVATIVES AND COMPOSITIONS AND METHOD OF USE THEREOF

BACKGROUND OF THE INVENTION (a) Field of the Invention

The invention relates to novel substituted 2-azabicy-clo-[2.2.2]octane derivatives, to compositions containing the same, and to the method of use thereof in the treatment of central nervous system disorders.

(b) A number of know antipsychotic drugs are disclosed in the art which have been shown to share a selective, high affinity for sigma receptors, which are sites where psychotomimetic opiates, such as (+)-pentazocine and N-allylnormetazocine, act. It has been suggested that the antipsychotic behavioral profile of these antipsychotic drugs can be attributed to their role as competitive antagonists of sigma receptor binding and that a systematic screen for drugs that block sigma receptors may provide a valuable strategy for identifying novel antipsychotic agents. Additionally, it has been shown that the relative potencies of these agents studied in vivo correspond well with their relative binding affinities obtained in vitro. See, for example, Synder and Largent, J. Neuropsychiatry 1989, 1(1), 7-15; Largent, et al., Eur. J. Pharmacol. 1988, 155, 345-347; Deutsch, et al., Clinical Neuropharmacology 1988, 11(2), 105-119; Tayler, et al., Drug Development Research 1987, 11, 65-70; Ferris, et al., Life Sciences 1986, 38(25), 2329-2337; and Su, et al., Neuroscience Letters 1986. 71, 224-228.

(b) Information Disclosure Statement

Moffett, U.S. Pat. No. 3,422,092, issued Jan. 14, 1969, discloses novel 2-carbamoyl and 2-lower-alkylcarbamoyl-2-azabicyclo[2.2.2]octanes which are said to be useful as central nervous system stimulants and lower-alkyl 2-azabicyclo[2.2.2]octane-3-carboxylates which are said to be useful as sedatives and diuretic agents.

Moffett, U.S. Pat. No. 3,497,518, issued Feb. 24, 1970, discloses novel N-(1-alkyl-4-piperidinyl)-2-azabicyclo[2.2.2]-octanes which are said to be useful as central nervous system stimulants.

Fonken, et al., U.S. Pat. No. 3,741,973, issued Jun. 26, 1973, disclose 2-benzoyl-2-azabicyclo[2.2.2]octane as an intermediate and 2-benzoyl-2-azabicyclo[2.2.2]octan-5-one and -5-ol, and 2-benzoyl-2-azabicyclo[2.2.2]octan-6-one and -6-ol as final products. The final products are said to be useful as central nervous system stimulants. A substantially similar disclosure can be found in Fonken, et al., U.S. Pat. No. 3,780,022, issued Dec. 18, 1973.

Michne, U.S. Pat. No. 4,180,667, issued Dec. 25, 1979, discloses, as intermediates, 2-$R_1$-3-(4-$R_2$-3-$R_2''$-5-$R_2'$-6-$R_2'''$-benzyl)-4-$R_3$-5-$R_4$-7-Y'-2-azabicyclo[2.2.-2]oct-5-enes wherein $R_1$ is hydrogen, lower-alkyl, lower-alkanoyl (only when $R_4$ is hydrogen), lower-alkenyl, lower-alkynyl, halo-lower-alkenyl, cycloalkyl, cycloalkyl-lower-alkyl, 2- or 3-furylmethyl, or such 2- or 3-furylmethyl substituted on the unsubstituted ring carbon atoms by from one to three methyl groups, phenyl-lower-alkyl, or phenyl-lower-alkyl substituted in the phenyl ring by from one to two members of the group consisting of halogen (including bromine, chlorine and fluorine), lower-alkyl, hydroxy, lower-alkanoyloxy, lower-alkoxy, lower-alkylmercapto, trifluoromethyl, amino, lower-alkanoylamino or a single methylenedioxy attached to adjacent carbon atoms;

$R_2$, $R_2'$, $R_2''$ and $R_2'''$ are each hydrogen, or three of them are hydrogen and the fourth is halogen (including bromine, chlorine or fluorine), lower-alkyl, hydroxy, lower-alkanoyloxy, lower-alkoxy, lower-alkylmercapto, trifluoromethyl, nitro, amino, lower-alkanoylamino, lower-alkoxycarbonylamino or phenyl, or two of the adjacent such groups together are methylenedioxy;

$R_3$ is hydrogen or lower-alkyl;

$R_4$ is hydrogen, lower-alkyl, lower-alkoxy-lower-alkyl, hydroxy-lower-alkyl, lower-alkylthio-lower-alkyl, lower-alkylsulfinyl-lower-alkyl, phenylthio-lower-alkyl, phenylsulfinyl-lower-alkyl, lower-alkenyl or halo-lower-alkyl, or $R_3$ and $R_4$ together are divalent lower-alkylene, —$(CH_2)_n$—, where n is one of the integers 3 or 4; and Y' is carboxy, cyano, carbo-lower-alkoxy, COO-lower-alkylene-cycloalkyl, COO-lower-alkylene-phenyl or lower-alkanoyl.

Ezer, et al., U.S. Pat. No. 4,563,464, issued Jan. 7, 1986, disclose 2-azabicyclo[2.2.2]octane derivatives of the formula:

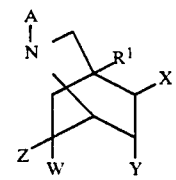

wherein:

A is hydrogen, alkoxycarbonyl having from one to four carbon atoms in the alkoxy group, phenylalkoxycarbonyl having from one to four carbon atoms in the alkoxy moiety, alkyl having from one to six carbon atoms, aralkyl containing from one to four carbon atoms in the alkyl moiety or substituted acyl;

$R_1$ is hydrogen or alkyl having from one to four carbon atoms;

Z is hydrogen or halogen;

X is hydrogen or halogen;

Y is hydrogen or;

X and Y together represent a C—C bond;

W is alkoxycarbonyl having from one to four carbon atoms in the alkoxy moiety, cyano, carboxamido or haloformyl; or if X stands for halogen, W and Y together represent a —$CO_2$— group.

The compounds are said to possess immunosuppressive, anticonvulsive, vasodilating and gastric acid secretion inhibiting properties.

Hartman, et al., U.S. Pat. No. 4,808,718, issued Feb. 28, 1989, disclose a series of substituted 2-azabicyclo[2.2.2]oct-2-ene dicarboxylates which are said to be useful as calcium entry blockers.

Michne, J. Org. Chem. 1976, 41(5), 894-896, discloses, as an intermediate, 3-benzyl-8-ethyl-2-methyl-2-azabicyclo[2.2.2]-oct-7-ene-6-carboxylate.

Buchi, et al., J. Am. Chem. Soc. 1966, 88(13), 3099-3109 disclose methyl 2-benzyl-7-cyano-2-azabicyclo[2.2.2]octane-6-carboxylate hydrochloride without an indication of utility.

SUMMARY OF THE INVENTION

The invention relates to a compound of Formula I:

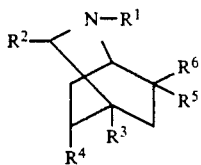

wherein:
R[1] is hydrogen, lower-alkyl or phenyl-lower-alkyl;
R[2] is lower-alkyl or phenyl-lower-alkyl;
R[3] is hydrogen or lower-alkyl;
R[4] is lower-alkylidene or lower-alkyl; or R[3] and R[4] together are —(CH$_2$)$_n$— wherein n is an integer from three to five;
R[5] is lower-alkoxycarbonyl, hydroxylower-alkyl, carboxy, or lower-alkanoyl; and
R[6] is hydrogen, lower-alkoxycarbonyl, hydroxylower-alkyl, lower-alkylthio or lower-alkyl;
or a pharmaceutically acceptable acid-addition salt thereof; with the proviso that when R$_6$ is lower-alkoxycarbonyl, R[5] must be lower-alkoxycarbonyl.

The compounds of the present invention bind with high affinity to sigma receptors and are thus useful in the treatment of central nervous system disorders.

Preferred compounds of Formula I above are those wherein
R[1] is hydrogen, methyl or phenylmethyl;
R[2] is methyl or phenylmethyl;
R[3] is hydrogen or lower-alkyl;
R$_4$ is ethylidene or lower-alkyl, or R[3] and R[4] together are —(CH$_2$)$_4$—;
R[5] is lower-alkoxycarbonyl, hydroxylower-alkyl, or lower-alkanoyl; and
R[6] is hydrogen, lower-alkoxycarbonyl, lower-alkylthio, or lower-alkyl.

Particularly preferred compounds of Formula I above are those wherein:
R[1] is hydrogen, methyl or phenylmethyl;
R[2] is methyl or phenylmethyl;
R[3] is hydrogen or methyl;
R[4] is ethylidene, methyl, ethyl or isopropyl, or R[3] and R[4] together are —(CH$_2$)$_4$—;
R[5] is lower-alkoxycarbonyl, hydroxylower-alkyl or lower-alkanoyl; and R[6] is hydrogen, lower-alkoxycarbonyl, lower-alkylthio or lower-alkyl.

The invention further relates to pharmaceutical compositions which comprise a compound of Formula I together with a pharmaceutically acceptable carrier, adjuvant, diluent or vehicle.

The invention further relates to a method for the treatment of central nervous system disorders, especially psychoses, which comprises administering to a patient in need of such treatment an effective amount of a compound of Formula I.

DETAILED DESCRIPTION INCLUSIVE OF PREFERRED EMBODIMENTS

The term lower-alkyl as used herein means linear or branched hydrocarbon chains having one to about four carbon atoms and thus includes methyl, ethyl, propyl, isopropyl, n-butyl, secbutyl, and the like.

The term lower-alkoxy as used herein means linear or branched alkyloxy substituents having one to about four carbon atoms and thus includes methoxy, ethoxy, propoxy, isopropoxy, butoxy, sec-butoxy, and the like.

The term lower-alkylidene as used herein means linear or branched hydrocarbon chains having two to about four carbon atoms and thus includes ethylidene, propylidene, isopropylidene, secbutylidene and the like.

The term hydroxylower-alkyl as used herein means linear or branched hydrocarbon chains having one to about four carbon atoms substituted by a hydroxy group at the C1 carbon atom and thus includes hydroxymethyl, 1-hydroxyethyl, 1-hydroxy-1-methylethyl and the like.

The term lower-alkanoyl as used herein means linear or branched hydrocarbon chains having two to about four carbon atoms and thus includes acetyl, propionyl, isobutyryl and the like.

The term halogen or halo as used herein means bromine, chlorine, iodine, or fluorine.

The synthesis of compounds of the invention wherein R[5] is lower-alkoxycarbonyl and R[6] is hydrogen may be outlined as shown in Scheme A.

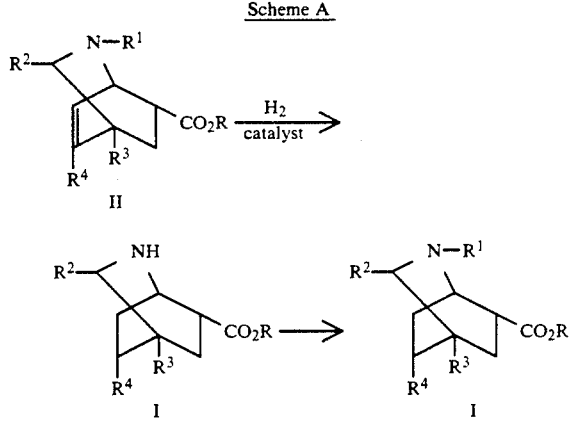

Scheme A

A suitably substituted lower-alkyl 2-azabicyclo[2.2.2]oct-7-ene-6-carboxylate of Formula II (R=lower-alkyl and R[1]=CH$_2$Ph) or acid-addition salt thereof, e.g. the hydrochloride, is hydrogenated at a hydrogen pressure of from about 15 psi to about 50 psi, in the presence of a catalyst, such as palladium on carbon, in an alcoholic solvent, such as ethanol, to produce a lower-alkyl 2-azabicyclo[2.2.2]octane-6-carboxylate of Formula I wherein R[1] is hydrogen. An appropriate R[1] substituent is then reintroduced into the compounds of Formula I by treating the compound of Formula I or acid-addition salt thereof, e.g. the hydrochloride, wherein R[1] is hydrogen (a) with an excess of formaldehyde and an excess of a base, preferably triethylamine, in an alcoholic solvent, such as ethanol, in the presence of hydrogen gas at a hydrogen pressure in the range of from about 15 psi up to about 50 psi to produce a compound of Formula I wherein R[1] is methyl; or (b) with an appropriate alkylating agent, e.g. R[1]X wherein X is chlorine, bromine or iodine, in the presence of an excess of a base, such as potassium carbonate, in a solvent, such as acetonitrile, at a temperature in the range of from about 25° C. up to the boiling point of the solvent used. It should be noted, however, that in the compounds of Formula II wherein R[1] is benzyl and R[4] is isopropyl only debenzylation occurs under the above-described reaction conditions to produce an appropriately substituted lower-alkyl 2-azabicyclo[2.2.2]oct-7-ene-6-carboxylate of Formula II' (R[1]=hydrogen, R[4]=isopropyl). This derivative or an acid-addition salt thereof, e.g. the hydrochloride, can then be hydrogenated in a Parr hydrogenator at a hydrogen pressure of about 25 psi to about 45 psi, in the presence of a catalyst, such as platinum oxide, in an acidic solvent, such as acetic acid, to produce an appropriately substituted lower-alkyl 2-azabicyclo[2.2.2]octane-6-carboxylate of Formula I ($R^1$=hydrogen, $R^4$=isopropyl). Alternatively, the latter compound can be prepared directly by the hydrogenation of a compound of the Formula II, wherein $R^1$ is benzyl and $R^4$ is isopropyl, in the presence of a catalyst, such as platinium oxide, in an acidic solvent, such as acetic acid. An appropriate $R^1$ substituent can then be reintroduced into the compounds of Formula I wherein $R^1$ is hydrogen and $R^4$ is isopropyl by the procedures described above. It will of course be appreciated that the compounds of the Formula II wherein $R^1$ is other than benzyl can be hydrogenated as described hereinabove to afford directly the compounds of the Formula I wherein $R^1$ is other than hydrogen or benzyl.

The synthesis of compounds of the invention wherein $R^5$ is lower-alkoxycarbonyl and $R^6$ is other than hydrogen may be outlined as shown in Scheme B.

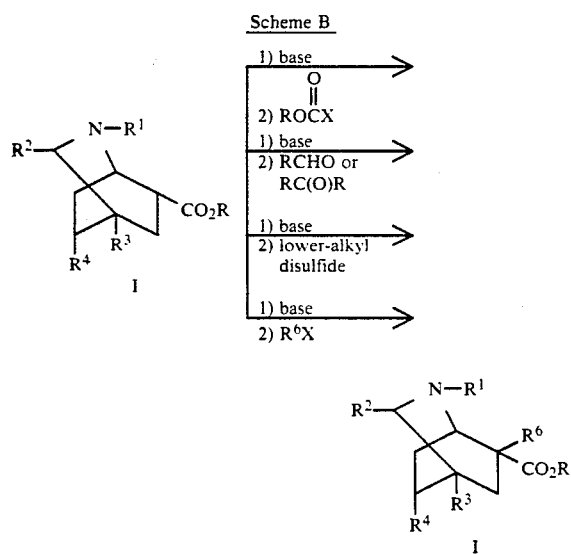

A suitably substituted lower-alkyl 2-azabicyclo[2.2.2]octane-6-carboxylate of Formula 1 wherein $R^6$ is hydrogen and $R^5$ is lower-alkoxycarbonyl is treated with an excess of a) an appropriate lower-alkyl haloformate, ROC(O)X' wherein R is lower-alkyl and X' is halogen, preferably a chloroformate; b) an appropriate aldehyde, RCHO, or ketone, RC(O)R; c) an appropriate lower-alkyl disulfide; or d) an appropriate lower-alkyl halide, $R^6$X, wherein $R^6$ is lower-alkyl, in the presence of an excess of a base, preferably lithium diisopropylamide, in a solvent, such as tetrahydrofuran, at a temperature in the range of about $-78°$ C. up to about $25°$ C., to produce compounds of Formula I wherein $R^6$ is a) lower-alkoxycarbonyl; b) hydroxylower-alkyl; c) lower-alkylthio; or d) lower-alkyl.

The synthesis of compounds of the invention wherein $R^6$ is other than lower-alkoxycarbonyl and $R^5$ is hydroxylower-alkyl may be outlined as shown in Scheme C.

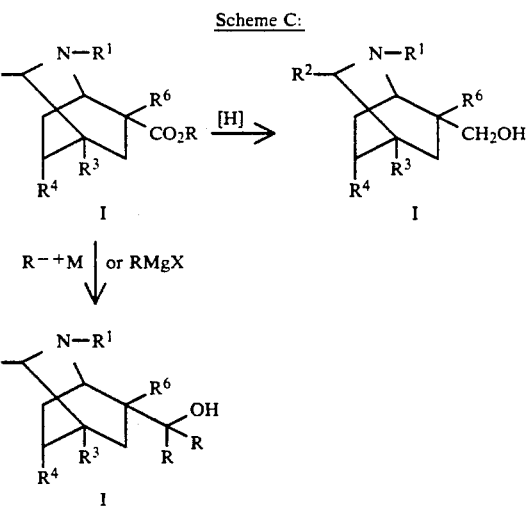

A suitably substituted compound of Formula I wherein $R^6$ is other than lower-alkoxycarbonyl and $R^5$ is lower-alkoxycarbonyl is treated with an excess of an appropriate reducing agent, e.g. lithium aluminum hydride, in a solvent, such as ether, at a temperature in the range of about $25°$ C. up to the boiling point of the solvent used to produce compounds of Formula I wherein $R^5$ is hydroxymethyl. Alternatively, the suitably substituted compound of Formula I wherein $R^6$ is other than alkoxycarbonyl and $R^5$ is lower-alkoxycarbonyl can be treated with an excess of an organometallic reagent, $R^{-+}M$, or with an appropriate Grignard Reagent, RMgX, wherein R is lower-alkyl, M is an alkali metal, such as lithium, and X is chlorine, bromine, or iodine in a solvent, such as ether, at a temperature in the range of $25°$ C. up to the boiling point of the solvent used to produce compounds of Formula I wherein $R^5$ is $C(R)_2OH$. It should be noted however, that when $R^1$ is phenylmethyl, $R^2$, $R^3$, $R^4$ and $R^6$ are methyl, and $R^5$ is ethoxycarbonyl only one equivalent of methyl magnesium iodide adds to the $R^5$ lower-alkoxycarbonyl group to produce the corresponding compound of Formula I wherein $R^1$ is phenylmethyl, $R^2$, $R^3$, $R^4$ and $R^6$ are methyl, and $R^5$ is acetyl.

The compounds of Formula I wherein $R^6$ is other than lower-alkoxycarbonyl and $R^5$ is carboxy or lower-alkanoyl may be prepared as outlined in Scheme D.

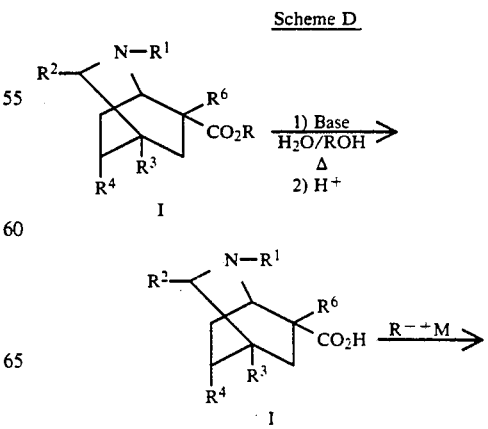

-continued
Scheme D

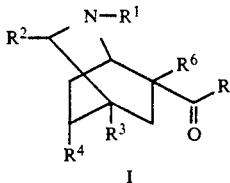

A suitably substituted compound of Formula I wherein $R^6$ is other than lower-alkoxycarbonyl and $R^5$ is lower-alkoxycarbonyl is treated with an excess of a base, such as sodium hydroxide, in a water/alcohol solvent mixture, e.g. water ethanol, at a temperature in the range of 25° C. up to the boiling point of the solvent mixture used to produce a compound of Formula I wherein $R^5$ is carboxy. The compound of Formula I wherein $R^5$ is carboxy can then be treated with an excess of an appropriate organometallic reagent, $R^{-+}M$, preferably a lower-alkyl lithium, in the presence of a solvent, such as ether, at a temperature of about 0° C. to produce compounds of the Formula I wherein $R^5$ is lower-alkanoyl.

In those instances wherein a compound of Formula I wherein $R^4$ is lower-alkylidene is desired it is convenient to proceed as shown in Scheme E.

Scheme E

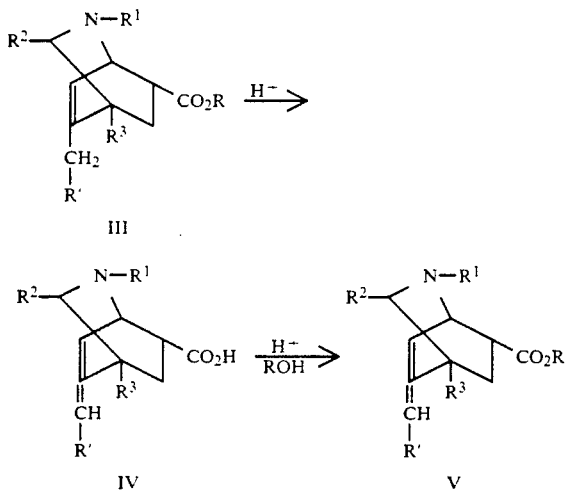

A suitably substituted lower-alkyl 2-azabicyclo[2.2.2]oct-7-ene-6-carboxylate of Formula III or acid-addition salt thereof, e.g. the hydrochloride, wherein R' is lower-alkyl of one to three carbon atoms is treated with an excess of an acid, such as hydrobromic acid, additionally in the presence of an excess of a second acid, such as acetic acid, at a temperature in the range of about 25° C. up to the boiling point of the acid mixture used to produce a carboxylic acid of Formula IV (Formula I wherein $R^4$ is lower-alkylidene and $R^5$ is carboxy). The carboxylic acid of Formula IV or acid-addition salt thereof, e.g. the hydrobromide, can then be treated with an excess of a gaseous acid, such as hyrochloric acid, in an alcoholic solvent, such as ethanol, at a temperature in the range of 25° C. up to the boiling point of the solvent used to produce a compound of Formula V (Formula I wherein $R^4$ is lower-alkylidene and $R^5$ is lower-alkoxycarbonyl). The compound of Formula V wherein $R^4$ is lower-alkylidene can then undergo the transformations described above to prepare the corresponding compounding of Formula I with various $R^5$ and $R^6$ substituents.

The suitably substituted lower-alkyl 2-azabicyclo[2.2.2]-oct-7-ene-6-carboxylates of Formulas II and III, required for the synthesis of the compounds of Formula I, can be prepared as outline in Scheme F.

Scheme F

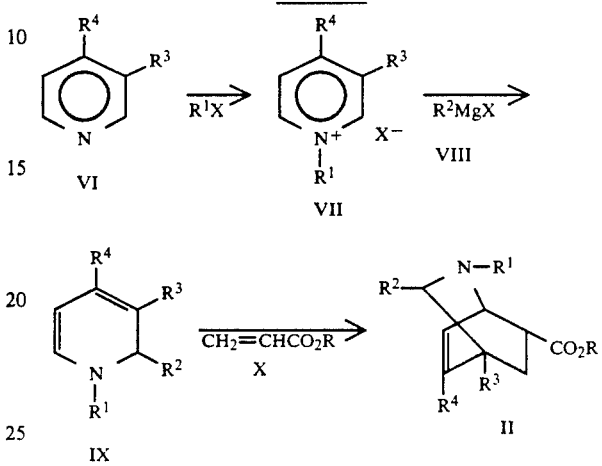

A suitably substituted pyridine derivative VI is treated with an appropriate alkylating agent, $R^1X$, in an alcoholic solvent, such as isopropanol, or a non-alcoholic solvent such as acetonitrile at a temperature in the range of from about 25° C. up to the boiling point of the solvent used, to afford a pyridinium salt of the Formula VII. The pyridinium salt (VII) can be treated with an excess of an appropriate Grignard reagent (VIII), in a solvent, such as ether, at a temperature in the range of from about 0° C. up to about 35° C. to afford the 1,2-dihydropyridine (IX). The 1,2-dihydropyridine (IX) can then be treated with a suitable lower-alkyl acrylate (X), in a solvent, such as toluene, at a temperature up to the boiling point of the solvent used to afford the lower-alkyl 2-azabicyclo[2.2.2]oct-7-ene-6-carboxylates of Formula II or Formula III (Formula II wherein $R^4$ is $CH_2R'$).

The appropriately substituted lower-alkyl haloformate (ROC(O)X'), aldehyde (RCHO), ketone (RC(O)R), lower-alkyl disulfide, lower-alkyl halide ($R^6X$), organometallic reagent ($R^-M^+$), Grignard reagent (RMgX), pyridine (VI), alkylating agent ($R^1X$), Grignard reagent ($R_2MgX$) and lower-alkyl acrylate (X) are either commercially available or can be prepared by procedures well known in the art.

The compounds of Formula I are useful both in the free base form and in the form of acid-addition salts, and, both forms are within the purview of the invention. The acid-addition salts are often a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial properties inherent in the free base are not vitiated by side effects ascribable to the anions. In practicing the present invention it is convenient to use the free base form or the hydrochloride, hydrobromide, fumarate, toluenesulfonate, methane-sulfonate or maleate salts. However, other appropriate pharmaceutically acceptable salts within the scope of the invention are those derived from other mineral acids and organic acids. The acid-addition salts of the basic compounds are prepared by standard procedures well known in the art which include, but are not limited thereto, dissolving the free base in an aqueous alcohol solution containing the appropriate acid and isolating the salt by evaporating the solution, or by reacting the free base and an acid in an organic solvent, in which case the salt separates directly, is precipitated with a second organic solvent or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed for purposes of purification or identification, or when it is used as an intermediate in preparing a medicinally acceptable salt by ion exchange procedures.

The structures of the compounds of the invention were established by the mode of synthesis, by elemental analysis, and by infrared, nuclear magnetic resonance and mass spectroscopy. The course of the reactions and the identity and homogeneity of the products were assessed by one or more of thin layer chromatography (TLC), high pressure liquid chromatography (HPLC), or gas-liquid chromatography (GLC).

The following examples will further illustrate the invention without, however, limiting it thereto. The abbreviation HCl stands for hydrochloric acid, MgSO$_4$ stands for magnesium sulfate, THF stands for tetrahydrofuran, NH$_4$Cl stands for ammonium chloride, Na$_2$SO$_4$ stands for sodium sulfate, K$_2$CO$_3$ stands for potassium carbonate, CH$_2$Cl$_2$ stands for dichloromethane, and NaOH stands for sodium hydroxide.

EXAMPLE 1

(a)

A mixture of 3,4-lutidine (112 mL, 1.0 mole), benzyl chloride (115 mL, 1.0 mole) and isopropanol (500 mL) was refluxed under nitrogen for 5 hours and then was stirred at room temperature for 60 hours. The mixture was diluted with ether and the resulting white precipitate was filtered and dried to afford 178.3 g (76%) of N-(phenylmethyl)-3,4-dimethylpyridinium chloride.

(b)

A solution of methyl iodide (112 mL, 1.8 mole) in ether (225 mL) was added dropwise to a suspension of magnesium turnings (44 g, 1.8 mole) in ether (225 mL) under nitrogen over a period of 1 hour. The mixture was stirred at room temperature for 1 hour, transferred into a 1000 mL addition funnel and then was added to a suspension of N-(phenylmethyl)-3,4-dimethylpyridinium chloride (350.7 g, 1.5 mole) in ether (1500 mL) under a nitrogen atmosphere. The reaction mixture was stirred at room temperature for 24 hours and was then poured into a solution of saturated ammonium chloride (3 L). The organic layer was separated and the aqueous layer was extracted with ether (1000 mL). The combined ether layers were washed with water (500 mL), then brine (500 mL) and were dried over sodium sulfate and potassium carbonate. The solvent was removed in vacuo to afford 284.1 g (76%) of 1,2-dihydro-N-(phenylmethyl)-2,3,4-trimethylpyridine as an amber oil.

(c)

A solution of 1,2-dihydro-N-(phenylmethyl)-2,3,4-trimethylpyridine (284.1 g, 1.14 mole) in toluene (3000 mL) under nitrogen was treated with ethyl acrylate (162 mL, 1.5 mole). The mixture was refluxed for 21 hours and the solvent was removed in vacuo. The residue was dissolved in ethanol (300 mL), treated with 10N ethanolic HCl and diluted with ether. A precipitate formed, which was collected by filtration and recrystallized from ethanol (150 mL)/ether (1400 mL) to afford 117.5 g (22%) of ethyl 3,4,8-trimethyl-2-(phenylmethyl)-2-azabicyclo[2.2.2]-oct-7-ene-6-carboxylate hydrochloride as a white powder, m.p. 184°–186° C. The mother liquor from the above recrystallization was treated with concentrated ammonium hydroxide (30 mL) and water (500 mL). The organic layer was separated, washed with brine and dried over potassium carbonate. The solvent was removed in vacuo and the residue was purified by column chromatography on silica eluting with ethyl acetate/hexane (25/75). The residue was dissolved in ethanol (50 mL), treated with 10.5N ethanolic HCl (10 mL) and diluted with ether (1200 mL). The product was collected by filtration and recrystallized from ethanol/ether to afford an additional 131.2 g of the product for a total yield of 47%.

(d)

A mixture of ethyl 3,4,8-trimethyl-2-(phenylmethyl)-2-azabicyclo[2.2.2]-oct-7-ene-6-carboxylate hydrochloride (17.4 g, 49.7 mol), 10% palladium on carbon (1.7 g) and ethanol (200 mL) was hydrogenated on a Parr hydrogenator at 50 psi for 6 hours. The mixture was removed from the Parr hydrogenator, cooled to 0° C. and triethylamine (7.0 mL, 50 mmol), followed by 37% formaldehyde (4.1 mL, 55 mmol) were added. The mixture was then placed back on the Parr hydrogenator at 50 psi for 1 hour. The reaction mixture was removed from the Parr hydrogenator, the catalyst was removed by filtration and the solvent was removed in vacuo. The residue was dissolved in water, basified with concentrated ammonium hydroxide (20 mL) and extracted with ether (3×300 mL). The combined organic layers were washed with brine (50 mL), dried over potassium carbonate and concentrated in vacuo to afford 11.5 g (96%) of ethyl 2,3,4,8-tetramethyl-2-azabicyclo[2,2,2]-octane-6-carboxylate as a pale yellow oil.

(e)

To a solution of diisopropylamine (3.0 mL, 22 mmol) in THF (34 mL) at 0° C. under nitrogen was added n-BuLi (8.8 mL, 22 mmol, 2.5M in hexanes). A solution of ethyl 2,3,4,8-tetramethyl-2-azabicyclo[2.2.2]octane-6-carboxylate (4.8 g, 20 mmol) in THF (46 mL) was added to the mixture and the reaction was stirred at 0° C. for 1 hour. Ethyl chloroformate (2.3 mL, 24 mmol) in THF (3 mL) was then added and the mixture was stirred for 15 minutes. The reaction mixture was diluted with saturated ammonium chloride and partitioned between water and ether. The aqueous layer was extracted with ether (2X) and the combined organic layers were dried over anhydrous MgSO$_4$. The solvent was removed in vacuo and the residue was purified by column chromatography on silica gel eluting with ether/hexane (15/85) to afford 3.9 g (63%) of diethyl 2,3,4,8-tetramethyl-2-azabicyclo-[2.2.2]octane-6,6-dicarboxylate as a yellow oil.

EXAMPLE 2

(a)

A mixture of ethyl 3,4,8-trimethyl-2-(phenylmethyl)-2-azabicyclo[2.2.2]oct-7-ene-6-carboxylate hydrochloride (26.5 g, mmol), 10% palladium on carbon (2.6 g) and ethanol (200 mL) were placed on a Parr hydrogenator at 50 psi for 3.5 hours. The catalyst was removed by filtration and the solvent was removed in vacuo to afford crude ethyl 3,4,8-trimethyl-2-azabicyclo[2.2.2]octane-6-carboxylate hydrochloride as a yellow oil, which was used directly in the next step.

(b)

A mixture of the above crude product (approximately 75 mmol), potassium carbonate (104 g, 0.75 mol), benzyl chloride (8.6 mL, 75 mmol) and acetonitrile (500 mL) were refluxed under nitrogen for 24 hours. The reaction mixture was filtered and the solvent was removed in vacuo to afford 22.4 g (93%) of ethyl 3,4,8-trimethyl-2-(phenylmethyl)-2-azabicyclo[2.2.2]octane-6-carboxylate as a golden oil. The product was dissolved in ethanol, treated with 5N ethereal HCl and diluted with ether to afford the hydrochloride salt as a white powder, m.p. 207°–208.5° C. when recrystallized from ethanol/ether (1/7).

(c)

To a solution of diisopropylamine (13.2 mL, 94 mmol) in THF (175 mL) at −60° C. under nitrogen was added n-BuLi (36.2 mL, 4 mmol, 2.6M hexane). The mixture was stirred for 30 minutes, cooled to −78° C. and ethyl 3,4,8-trimethyl-2-(phenylmethyl)-2-azabicyclo[2.2.2]octane-6-carboxylate (26.8 g, 85 mmol) in THF (225 mL) was added. The mixture was stirred for 3 hours, then ethyl chloroformate (8.96 mL, 94 mmol) in THF (20 mL) was added dropwise. The mixture was stirred for 24 hours, quenched with saturated NH4Cl, and poured into water (1000 mL). The solution was extracted with ether (3X), and the organic layers were combined and dried over MgSO4. The ether layer was treated with charcoal and the solvent was removed in vacuo to afford 32.1 g (97%) of diethyl 3,4,8-trimethyl-2-(phenylmethyl)-2-azabicyclo-[2.2.2]octane-6,6-dicarboxylate as a golden oil. The product was dissolved in ether and treated with ethereal HCl to afford 24 g (66%) of the hydrochloride salt as a white solid, m.p. 160°–162° C.

EXAMPLE 3

(a)

Following a procedure similar to that described in Example 1(a), 415 g (89%) of N-(phenylmethyl)-4-ethylpyridinium chloride obtained from 4-ethylpyridine (214 g, 2.0 mol), benzyl chloride (253 g, 2.0 mol) and isopropanol (1200 mL). The product had a melting point of 157°–162° C.

(b)

Following a procedure similar to that described in Example 1(b), 1,2-dihydro-N,2-di(phenylmethyl)-4-ethylpyridine was obtained from N-(phenylmethyl)-4-ethylpyridinium chloride (163 g, 0.7 mol), magnesium turnings (34 g, 1.4 mol), benzyl chloride (177 g, 1.4 mol) and ether (1400 mL). The product was used directly in the next step without purification.

(c)

Following a procedure similar to that described in Example 1(c), 132 g (44%) of ethyl 8-ethyl-2,3-di(phenylmethyl)-2-azabicyclo[2.2.2]oct-7-ene-6-carboxylate hydrochloride, m.p. 197°–200° C., was obtained from 1,2-dihydro-N,2-di(phenylmethyl)-4-ethylpyridine of Example 3(b), toluene (1400 mL) and ethyl acrylate (154 mL, 1.4 mol).

(d)

A mixture of ethyl 8-ethyl-2,3-di(phenylmethyl)-2-azabicyclo[2.2.2]oct-7-ene-6-carboxylate (132 g, 0.31 mol) in 48% HBr (1300 mL) was refluxed for 30 minutes, then acetic acid (650 mL) was added and the mixture was refluxed for an additional 24 hours. A precipitate formed which was collected by filtration and washed with acetic acid/ether to afford 20.8 g of 2,3-di(phenylmethyl)-8-ethylidene-2-azabicyclo[2.2.2]octane-6-carboxylic acid hydrobromide, m.p. 251°–253° C. (dec.). Additional crops of the product were obtained by cooling the filtrate in an ice-bath and collecting the crystals that formed by filtration. A total of 69.8 g (50%) of the product was obtained in this manner.

(e)

To a suspension of 2,3-di(phenylmethyl)-8-ethylidene-2-azabicyclo[2.2.2]octane-6-carboxylic acid hydrobromide (52.0 g, 0.12 mol) in ethanol (500 mL) was bubbled HCl gas until a homogeneous solution was obtained. The mixture was then refluxed for 3 hours, diluted with ether and the solvent was removed in vacuo. The residue was dissolved in ethanol and triturated with water to afford a precipitate. The precipitate was collected by filtration and washed with ethanol/water (1/1) to afford 20.3 g (41%) of ethyl 2,3-di(phenylmethyl)-8-ethylidene-2-azabicyclo-[2.2.2]octane-6-carboxylate trihydrochloride hydrobromide as a white solid, m.p. 201°–203° C. when recrystallized from ethanol.

EXAMPLE 4

Following a procedure similar to that described in Example 1, parts a, b, and c, there was obtained:

(a)

N-Methyl-4-ethylpyridinium iodide (484 g, 97%) from 4-ethylpyridine (214 g, 2.0 mol), iodomethane (135 mL, 2.2 mol) and acetonitrile (500 mL).

(b)

1,2-Dihydro-N-methyl-2-(phenylmethyl)-4-ethylpyridine from N-methyl-4-ethylpyridinium iodide (175 g, 0.7 mol), magnesium turnings (24.3 g, 1.0 mol), benzyl chloride (115 mL, 1.0 mol) and ether (1500 mL). The product was used directly in the next step without purification.

(c)

Ethyl 3-(phenylmethyl)-8-ethyl-2-(methyl)-2-azabicyclo-[2.2.2]oct-7-ene-6-carboxylate hydrochloride (123.5 g, 50%), m.p. 192°–194° C. when recrystallized from ethanol/ether, from 1,2-dihydro-N-methyl-2-(phenylmethyl)-4-ethylpyridine, toluene (600 mL) and ethyl acrylate (200 mL, 1.8 mol).

(d)

A mixture of ethyl 3-(phenylmethyl)-8-ethyl-2-methyl-2-azabicyclo[2.2.2]oct-7-ene-6-carboxylate hydrochloride (23.2 g, 0.067 mol), ethanol (300 mL) and 10% palladium on carbon (1.0 g) was placed on a Parr hydrogenator at approximately 50 psi and was heated to 50° C. for 3 hours and 20 minutes. The catalyst was removed by filtration and the filtrate was concentrated in vacuo. The residue was dissolved in hot ethanol and cooled on an ice-bath. The precipitate which formed was collected by filtration and dried at 40° C. in vacuo to afford 17.2 g (73%) of ethyl 3-(phenylmethyl)-8-ethyl-2-methyl-2-azabicyclo[2.2.2]octane-6-carboxylate hydrochloride, m.p. 226°–227° C.

(e)

Ethyl 3-(phenylmethyl)-8-ethyl-2-methyl-2-azabicyclo[2.2.2]octane-6-carboxylate hydrochloride (14 g, 0.043 mol) was treated with ammonium hydroxide and extracted with ether. The ether extracts were washed with water, dried over anhydrous $MgSO_4$ and concentrated in vacuo to afford 13.0 g (0.045 mol) of the free base. The free base (13.0 g, 0.045 mol) in ether (140 mL) was then slowly added to a solution of methyllithium (75 mL, 0.135 mol, 1.8M ether) under a nitrogen atmosphere. The mixture was stirred for 45 minutes, then allowed to stand for 24 hours. The mixture was poured into ice/saturated $NH_4Cl$, the organic layer was separated and washed with brine. The organic layer was treated with charcoal, dried over anhydrous $MgSO_4$ and concentrated in vacuo to afford 10.4 g (72%) of 3-(phenylmethyl)-8-ethyl-2,α,α-trimethyl-2-azabicyclo[2.2.2]octane-6-methanol. The product was dissolved in ethanol and treated with ethereal HCl to afford 10.3 g (72%) of the hydrochloride salt as a white solid, m.p. 234°–236° C. when recrystallized from isopropanol/ether.

EXAMPLE 5

Following a procedure similar to that described in Example 1, parts a, b, and c, there was obtained:

(a)

N-(Phenylmethyl)-5,6,7,8-tetrahydroisoquinolinium bromide (97.6 g, 95%) as pale creamed colored crystals, from 5,6,7,8-tetrahydroisoquinoline (45 g, 338 mmol), benzyl bromide (578 g, 338 mmol) and isopropanol (450 mL).

(b)

N-(Phenylmethyl)-1-methyl-2,3,5,6,7,8-hexahydroisoquinoline (66.5 g, 84%) as a golden oil from N-(phenylmethyl)-5,6,7,8-tetrahydroisoquinolinium bromide (100.6 g, 330 mmol), magnesium turnings (9.7 g, 0.4 mol), methyl iodide (56.8 g, 0.4 mol) and ether (650 mL). The product was used directly in the next step without purification.

(c)

Ethyl 2,3,5,6,7,8-hexahydro-1-methyl-2-(phenylmethyl)-1H-3,8a-ethanoisoquinoline-10-carboxylate hydrochloride (40.0 g, 32%) as a white solid, m.p. 149°–151° C. when recrystallized from ethanol/ether, from N-(phenylmethyl)-1-methyl-2,3,5,6,7,8-hexahydroisoquinoline (66.5 g, 0.28 mol), toluene (600 mL) and ethyl acrylate (40 mL, 0.4 mol).

Following a procedure substantially similar to that described in Example 2, parts a and b, there was obtained:

(d)

Ethyl 2,3,4,4a,5,6,7,8-octahydro-1-methyl-1H-3,8a-ethanoisoquinoline-10-carboxylate hydrochloride from ethyl 2,3,5,6,7,8-hexahydro-1-methyl-2-(phenylmethyl)-1H-3,8a-ethanoisoquinoline-10-carboxylate hydrochloride (26.4 g, 70 mmol), ethanol (200 mL) and 10% palladium on carbon (1.0 g). The product was used directly in the next step without purification.

(e)

Ethyl 2,3,4,4a,5,6,7,8-octahydro-1-methyl-2-(phenylmethyl)-1H-3,8a-ethanoisoquinoline-10-carboxylate hydrochloride (24.2 g, 91%) as a white solid, m.p. 191°–193° C. when recrystallized from ethanol/ether, from ethyl 2,3,4,4a,5,6,7,8-octahydro-1-methyl-1H-3,8a-ethanoisoquinoline-10-carboxylate hydrochloride of Example 5d, acetonitrile (500 mL), benzyl bromide (8.1 mL, 70 mmol) and potassium carbonate (97 g, 700 mmol).

EXAMPLE 6

A solution of diisopropylamine (6.8 mL, 48 mmol) in THF (100 mL) was cooled to −70° C. and n-BuLi (17.6 mL, 44 mmol, 2.5M hexane) was added to afford lithium diisopropylamide (LDA). A solution of ethyl 2,3,4,8-tetramethyl-2-azabicyclo[2.2.2]octane-6-carboxylate (9.6 g, 40 mmol) in THF (50 mL) was then added dropwise to the solution of LDA and the mixture was stirred for 2.5 hours. Methyl disulfide (4.3 mL, 48 mmol) was then added to the reaction mixture and the mixture was slowly warmed to room temperature and was stirred for 16 hours. The mixture was poured into saturated $NH_4Cl$ (200 mL), the organic layer was separated and the aqueous layer was extracted with ether (2×200 mL). The organic layers were combined, dried over anhydrous $Na_2SO_4$ and concentrated in vacuo. The residue was purified by medium pressure liquid chromatography (10–15% ethyl acetate/hexane) to afford 9.2 g (81%) of ethyl 2,3,4,8-tetramethyl-6-(methylthio)-2-azabicyclo[2.2.2]octane-6-carboxylate. The product was dissolved in ether and treated with ethereal HCl to afford 6.5 g of the hydrochloride salt as a white powder, m.p. 143°–145° C. when recrystallized from ethyl acetate.

EXAMPLE 7

Methyl iodide (138.4 g, 0.98 mole) was added dropwise over 1.5 hours to magnesium turnings (23 7 g, 0.98 mole) in ether (300 mL). The solution was diluted to a total volume of 1 liter and was stirred at room temperature for 2 hours. The solution was filtered through a glass wool plug into a second flask under nitrogen and a solution of ethyl 3,4,8-trimethyl-2-(phenylmethyl)-2-azabicyclo[2.2.2]-octane-6-carboxylate (87.9 g, 0.28 mole) in ether (400 mL) was added over 2 hours. The mixture was stirred at room temperature for 1 hour, poured into a mixture of saturated $NH_4Cl$ (700 mL) and ice-water (1000 mL) and the organic layer was separated. The aqueous phase was extracted with ether (2×700 mL) and the combined organic layers were washed with water (2×500 mL), then brine (500 mL) and were dried over anhydrous $MgSO_4$. The solvent was removed in vacuo to afford 82.5 g (98%) α,α,3,4,8-pentamethyl-2-(phenylmethyl)-2-azabicyclo[2.2.2]octane-6-methanol. A small portion of the product (5.0 g)

was treated with ethereal HCl to afford the hydrochloride salt as a white solid, m.p. 221°-222° C. (dec) when recrystallized from ethanol/ether.

EXAMPLE 8

(a)

Following a procedure similar to that described in Example 6, 44.5 g (100%) of ethyl 2-(phenylmethyl)-3,4,6,8-tetramethyl-2-azabicyclo[2.2.2]octane-6-carboxylate was obtained as a brown oil from ethyl 3,4,8-trimethyl-2-(phenylmethyl)-2-azabicyclo[2.2.2]octane-6-carboxylate (42.5 g, 135 mmol), diisopropylamine (16.3 g, 162 mmol), n-BuLi (59.2 mL, 148 mmol), methyl iodide (10.9 mL, 175 mmol) and THF (575 mL). A small portion of the product was dissolved in ether and treated with ethereal HCl to afford the hydrochloride salt as a white solid, m.p. 193°-194° C. when recrystallized from ethanol/ether.

(b)

Following a procedure similar to that described in Example 7, 25.6 g (96%) of 1-[3,4,6,8-tetramethyl-2-(phenylmethyl) -2-azabicyclo[2.2.2]oct-6-yl]ethanone was obtained from ethyl 2-(phenylmethyl)-3,4,6,8-tetramethyl-2-azabicyclo[2.2.2]-octane-6-carboxylate (27.9 g, 84.7 mmol), methyl iodide (48.1 g, 339 mmol), magnesium turnings (8.2 g, 339 mmol) and ether (1000 mL). The product was dissolved in ether and treated with ethereal HCl to afford the hydrochloride salt as an off-white powder, m.p. 170°-172° C. (dec.) when recrystallized from THF/ether and dried in vacuo at 90° C. for 4 days.

EXAMPLE 9

Following a procedure similar to that described in Example 1, parts a, b and c, there was obtained:

(a)

N-(Phenylmethyl)-4-isopropylpyridinium chloride from 4-isopropylpyridine (129 mL, 1.0 mol), isopropanol (500 mL) and benzyl chloride (121 mL, 1.05 mol). The product was then dissolved in acetone (250 mL) and treated with sodium iodide. A precipitate formed which was collected by filtration to afford 214.6 g (87%) of N-(phenylmethyl)-4-isopropylpyridinium iodide as white crystals.

(b)

1,2-Dihydro-N-(phenylmethyl)-2-methyl-4-isopropylpyridine (161.4 g) as a greenish oil from N-(phenylmethyl)-4-isopropylpyridinium iodide (214 g, 0.86 mol), methyl iodide (62.2 mL, 1.0 mol), magnesium turnings (25.2 g, 1.05 mol), and ether (1.5 L).

(c)

Ethyl 3-methyl-8-isopropyl-2-(phenylmethyl)-2-azabicyclo[2.2.2]oct-7-ene-6-carboxylate hydrochloride (81.8 g, 26%) as white prisms, m.p. 194°-196° C. (dec.), from 1,2-dihydro-N-(phenylmethyl)-2-methyl-4-isopropylpyridine (161.4 g), toluene (900 mL) and ethyl acrylate (195 mL, 1.8 mol).

(d)

A mixture of ethyl 3-methyl-8-isopropyl-2-(phenylmethyl)-2-azabicyclo[2.2.2]oct-7-ene-6-carboxylate hydrochloride (23.2 g, 63.8 mmol), ethanol (200 mL) and 10% palladium on carbon (2.3 g) was placed on a Parr hydrogenator at 44 psi of hydrogen pressure for 4 hours. The catalyst was removed by filtration and the solvent was concentrated in vacuo to afford 17.6 g (100%) of ethyl 3-methyl-8-isopropyl-2-azabicyclo[2.2.-2]oct-7-ene-6-carboxylate hydrochloride as a white solid.

(e)

A mixture of ethyl-3-methyl-8-isopropyl-2-azabicyclo[2.2.2]oct-7-ene-6-carboxylate (21.4 g, 78 mmol), acetic acid (200 mL) and platinum oxide (2.1 g) was placed on a Parr hydrogenator at 44 psi of hydrogen pressure for 4¼ hours. The catalyst was removed by filtration and the solvent was removed in vacuo. The residue was dissolved in water, neutralized with NH$_4$OH to a pH of 10 and the mixture was extracted with CH$_2$Cl$_2$ (3×50 mL). The organic layers were combined, washed with brine and dried over MgSO$_4$. The solvent was removed in vacuo to afford 18.1 g (97%) of ethyl 3-methyl-8-isopropyl-2-azabicyclo-[2.2.2]octane-6-carboxylate. The product was dissolved in ethanol and treated with 6.9N ethanolic HCl to afford 10.2 g of the hydrochloride salt as a white solid, m.p. 157.5°-158.5° C.

(f)

Following a procedure similar to that described in Example 2b, 31.6 g (98%) of ethyl 3-methyl-8-(isopropyl)-2-(phenylmethyl)-2-azabicyclo[2.2.2]octane-6-carboxylate was obtained from ethyl 3-methyl-8-(isopropyl)-2-azabicyclo[2.2.2]-octane-6-carboxylate (23.4 g, 97.8 mmol), acetonitrile (230 mL), benzyl chloride (12.9 mL, 0.11 mol) and K$_2$CO$_3$ (69.1 g, 0.5 mol). The product was dissolved in ethanol and treated with 6.9N ethereal HCl to afford 10.7 g of the hydrochloride salt as a white powder, m.p. 202°-204° C.

EXAMPLE 10

A solution of ethyl 2,3,4,8-tetramethyl-2-azabicyclo[2.2.2]octane-6-carboxylate (18.3 g, 76.5 mmol) in ether (200 mL) was added to a slurry of lithium aluminum hydride (5.8 g, 153 mmol) in ether (60 mL). The mixture was stirred for 1 hour, cooled to 0° C. and quenched by the sequential addition of water (5.8 mL), 15% NaOH (5.8 mL), and water (17.4 mL). The aluminum salts were removed by filtration and the filtrate was concentrated in vacuo to afford 14.8 g (98%) of 2,3,4,8-tetramethyl-2-azabicyclo[2.2.2]octane-6-methanol as a colorless oil. The product was dissolved in ether and treated with 4.9N ethereal.HCl to afford 9.1 g of the hydrochloride salt as a white solid, m.p. 158°-159° C.

EXAMPLE 11

(a)

A mixture of ethyl 3-methyl-8-isopropyl-2-(phenylmethyl)-2-azabicyclo[2.2.2]octane-6-carboxylate (32.9 g, 100 mmol), ethanol (150 mL), water (150 mL) and NaOH (4.8 g, 120 mmol) were refluxed for 18 hours. The solvent was removed in vacuo and the residue was diluted with water and washed with ether (1×50 mL). The aqueous layer was acidified with acetic acid (6.9 mL, 120 mmol) and extracted with CH$_2$Cl$_2$ (3×50 mL). The organic layers were combined, washed with brine, dried over MgSO$_4$ and concentrated in vacuo to afford 30.3 g (100%) of 3-methyl-8-isopropyl-2-(phenylmethyl)-2-azabicyclo[2.2.2]octane-6-carboxylic acid.

(b)

A solution of 3-methyl-8-isopropyl-2-(phenylmethyl)-2-azabicyclo[2.2.2]octane-6-carboxylic acid (30.1 g, 100 mmol) and ether (300 mL) was cooled to 0° C. and methyllithium (330 mL, 1.2N solution in ether) was added dropwise over 2 hours. The mixture was stirred for 1 hour at 0° C. and quenched by the addition of saturated NH$_4$Cl (100 mL). The mixture was poured into water (1 L), and the aqueous layer was separated and extracted with ether (1×200 mL). The ether extracts were combined, washed with brine, dried over MgSO$_4$ and concentrated in vacuo. The residue was purified by column chromatography on silica gel eluting with 25% ether/hexane to afford 14.3 g (48%) of 1-[3-methyl-8-isopropyl-2-(phenylmethyl)-2-azabicyclo[2.2.2]octan-6-yl]-ethanone. The product was treated with ethereal.HCl to afford 15.2 g of the hydrochloride salt as a white solid, m.p. 208.5°–210° C. (dec.) when recrystallized from ethanol/ether.

EXAMPLE 12

Following a procedure similar to that described in Example 2C, but substituting an appropriate aldehyde or ketone for ethylchloroformate, it is contemplated that the following compounds of Formula I listed in Table 1 can be prepared.

TABLE 1

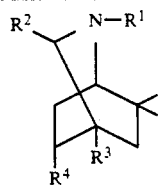

| Example | R$^1$ | R$^2$ | R$^3$ | R$^4$ | R$^5$ | R$^6$ |
|---|---|---|---|---|---|---|
| 12A | CH$_2$Ph | CH$_3$ | CH$_3$ | CH$_3$ | CO$_2$Et | CH$_2$OH |
| 12B | CH$_2$Ph | CH$_3$ | CH$_3$ | CH$_3$ | CO$_2$Et | CH(OH)CH$_3$ |
| 12C | CH$_2$Ph | CH$_3$ | CH$_3$ | CH$_3$ | CO$_2$Et | C(CH$_3$)(OH)CH$_3$ |

BIOLOGICAL TEST RESULTS

In standard biological test procedures, representative examples of the compounds of the invention have been found to bind with high affinity to sigma receptors, and are thus useful in the treatment of central nervous system disorders such as psychoses, dystonias, dyskinesias, Parkinson's syndrome, Huntington's chorea, Tourette syndrome and the like, especially psychoses, e.g. schizophrenic psychoses, manic depressive psychoses and the like.

The sigma receptor binding activity of representative compounds of the invention was demonstrated by following a procedure essentially as described by Hudkins and DeHaven-Hudkins, Life Sci. 1991, 49(17), 1229–1235.

Brain tissue was prepared from male Hartley guinea pigs (Hazelton Labs, Denver, Pa.) which were anesthetized with CO$_2$ and sacrificed by decapitation. All animal care and use procedures were in accord with the "Guide for the Care and Use of Laboratory Animals" (NIH Publ. No. 86-23, 1985). Homogenization was performed in 10 volumes (wt/vol) of 0.32M sucrose with a Brinkmann Polytron at setting 5, 30 sec. The homogenate was centrifuged at 900×g for 10 min at 4° C., and the supernatant was collected and centrifuged at 22,000×g for 20 min at 4° C. The pellet was resuspended in 10 volumes of Tris-HCl buffer (50 mM, pH 7.4), incubated at 37° C. for 30 min, and centrifuged at 22,000×g for 20 min at 4° C. Following this, the pellet was resuspended in Tris buffer and frozen in 5–10 mL aliquots corresponding to a tissue concentration of 100 mg/mL, at −70° C. Binding characteristics of the membranes were stable for at least one month when stored at −70° C.

On the day of the assay, membrane aliquots were thawed, resuspended in fresh Tris-HCl buffer and stored on ice until use. Each assay tube contained 100 μL of [$^3$H]-(+)-pentazocine at a final concentration of approximately 0.5 nM or 100 μL of [$^3$H]-di(2-tolyl)-guanidine (DTG) at a final concentration of approximately 4 nM, 100 μL of various concentrations of the compounds of interest, 500 μL of the tissue suspension and 300 μL of buffer to a final assay volume of 1 mL and a final tissue concentration of approximately 8 mg/tube, corresponding to approximately 0.15 mg protein/tube. Non-specific binding was defined by addition of a final concentration of 1 μM haloperidol to blank tubes for [$^3$H](+)-pentazocine assay or by addition of a final concentration of 10 μM haloperidol to blank tubes for [$^3$H]DTG assay. All tubes were incubated at 37° C. for 150 min in the [$^3$H](+)-pentazocine assay or at 25° C. for 90 min in the [$^3$H]DTG assay before termination of the reaction by rapid filtration over Whatman GF/B glass fiber filters that were presoaked in a solution of 0.5% polyethylenimine for at least 1 hr prior to use. Filters were washed with three 4 ml volumes of cold Tris-HCl buffer.

Following addition of scintillation cocktail, samples were allowed to equilibrate for at least 4 hr. The amount of bound radioactivity was determined by liquid scintillation spectrometry using a Beckman LS 5000 TA liquid scintillation counter with an efficiency for tritium of approximately 60%. The results are reported as a percent (%) inhibition of binding at 10 μM.

Scatchard parameters and inhibition constants (K$_i$ values) for the binding of test compounds were also calculated using the EBDA/LIGAND program (McPherson, J. Pharmacol. Meth. 1985, 14, 213–228), purchased from Elsevier/Biosoft, Inc The K$_i$ values are expressed as the mean of at least two separate determinations performed in triplicate.

The following Table summarizes the results obtained from the testing of representative compounds of the invention.

TABLE 2

| | [$^3$H] (+)−Pentazocine | | [$^3$H]DTG | |
|---|---|---|---|---|
| Example No. | Percent Inhibition | Ki (nM) | Percent Inhibition | Ki (nM) |
| 3e | 33 | — | 57 | — |
| 4e | 72 | 2958 | 75 | 2884 |
| 2b | — | 242 | — | 240 |
| 5e | 97 | 332 | — | 357 |
| 2c | 79 | 1188 | 79 | 1244 |
| 6 | 63 | 5953 | 75 | 2712 |
| 7 | 59 | 6064 | — | 6109 |
| 8a | — | 9825 | 29 | 6471 |
| 8b | 47 | 8882 | 65 | 4555 |
| 9e | 30 | — | 48 | — |
| 9f | — | 141 | — | 75.5 |
| 10 | 24 | — | 48 | — |
| 11b | 77 | 2619 | 86 | 1009 |

Representative compounds of the invention were tested in vivo in the apomorphine-induced climbing assay and the apomorphine-induced stereotypy assay using the following procedures.

Male, Swiss-Webster mice (Taconic Farms, Germantown, New York), weight 20-30 grams, were grouped housed in colony facilities for a minimum of two days prior to testing. The colony facility was maintained on a 12 hour light/dark cycle (light: 0600-1800 hours) with water and Agway Prolab 100 rat chow available ad libitum. Each mouse was given an injection of test compound i.p. followed immediately by a s.c. injection of apomorphine 5.5 mg/kg or vehicle. All drugs were administered in a volume of 10 ml/kg body weight. The mice were then placed in individual cylindrical stainless steel climbing cages; 14.5 cm tall, 12 cm in diameter, with walls consisting of 1/16" O.D. bars spaced 0.8-1.0 cm apart, and were allowed to habituate to this environment for 20 minutes. Rating of climbing and stereotypy occurred every 30 seconds for ten minutes (e.g. 20-30 minutes post drug treatment) by an observer blind to treatment. The scale used for climbing was simply the number of paws contacting the bars (0-4). The stereotypy scale used (0-3) was that described previously (Peuch et al. European Journal of Pharmacology 1978, 50, 291). Briefly, a (0) was scored for absence of any stereotypic behavior, infrequent stereotypic movements were scored as (1), a (2) was scored for permanent sniffing and a score of (3) indicated intense and continuous stereotypic behavior. Treatment means for the 10 minute totals were calculated for climbing and stereotypy. A Student's t-test was used to confirm a significant (P<0.05) increase in both behaviors following apomorphine treatment. Significant (P<0.05) antagonism as potentiation of the apomorphine-induced effect was identified using Dunnett's Test comparing each treatment group to apomorphine control using the computer program of Tallarida and Murray (Manual of Pharmacologic Calculation with Computer Programs, p. 145, Springer-Verlag, New York, 1987). A minimal effective dose (MED) for inhibition was determined for each parameter based on these analyses.

The following Table summarizes the results obtained from the in vivo testing of representative compounds of the invention.

TABLE 3

| Example No. | Apomorphine-induced climbing assay MED ($\mu$mol/kg) | Apomorphine-induced stereotypy assay MED ($\mu$mol/kg) |
| --- | --- | --- |
| 2b | 317 | 951 |
| 9f | 304 | 304 |

The compounds of the invention can be prepared for pharmaceutical use by conventional pharmaceutical procedures that are well known in the art; that is, by formulating a pharmaceutical composition which comprises compounds of the invention or their pharmaceutically acceptable salts together with one or more physiologically acceptable carriers, adjuvants, diluents or vehicles, for oral administration in solid or liquid form, parenteral administration, topical administration or aerosol inhalation administration, and the like.

Solid compositions for oral administration include compressed tablets, pills, powders and granules. In such solid compositions, the active compound is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilizing, preserving, wetting, emulsifying and dispersing agents.

Preparations according to the invention for topical administration or aerosol inhalation administration include dissolving or suspending a compound of the invention in a pharmaceutically acceptable vehicle such as water, aqueous alcohol, glycol, oil solution or oil-water emulsion, and the like.

If desired, the compounds of the invention can further be incorporated into slow release or targeted delivery systems such as polymer matrices, liposomes, and microspheres.

The percentage of active component in such compositions may be varied so that a suitable dosage is obtained. The dosage administered to a particular patient is variable depending upon the clinician's judgment using as criteria: The route of administration, the duration of treatment, the size and physical condition of the patient, the potency of the active component and the patient3 s response thereto. An effective dosage amount of the active component can thus readily be determined by the clinician after a consideration of all criteria and using his best judgment on the patient's behalf.

We claim:

1. A compound of the formula:

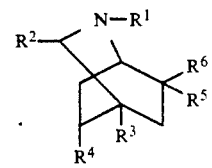

wherein:

R$^1$ is hydrogen, lower-alkyl or phenyl-lower-alkyl;

R$^2$ is lower-alkyl or phenyl-lower-alkyl;

R$^3$ is hydrogen or lower-alkyl;

R$^4$ is lower-alkylidene or lower-alkyl; or R$^3$ and R$^4$ together are —(CH$_2$)$_n$— wherein n is an integer from three to five;

R$^5$ is lower-alkoxycarbonyl, hydroxylower-alkyl, carboxy, or lower-alkanoyl; and R$^6$ is hydrogen, lower-alkoxycarbonyl, hydroxylower-alkyl, lower-alkylthio, or lower-alkyl;

or a pharmaceutically acceptable acid-addition salt thereof; with the proviso that when $R^6$ is lower-alkoxycarbonyl, $R^5$ must be lower-alkoxycarbonyl.

2. A compound according to claim 1 wherein $R^5$ is lower-alkoxycarbonyl, hydroxylower-alkyl, or lower-alkanoyl; and $R^6$ is hydrogen, lower-alkoxycarbonyl, lower-alkylthio, or lower-alkyl.

3. A compound according to claim 2 wherein $R^3$ is hydrogen or lower-alkyl; and $R^4$ is ethylidene or lower-alkyl; or $R^3$ and $R^4$ together are —(CH$_2$)$_4$—.

4. A compound according to claim 3 wherein $R^2$ is methyl or phenylmethyl

5. A compound according to claim 4 wherein $R^1$ is hydrogen, methyl, or phenylmethyl.

6. A compound according to claim 5 wherein $R^3$ is hydrogen or methyl; and $R^4$ is ethylidene, methyl, ethyl, or isopropyl, or $R^3$ and $R^4$ together are —(CH$_2$)$_4$—.

7. A compound according to claim 6 wherein $R^6$ is hydrogen, ethoxycarbonyl, methylthio or methyl.

8. A compound according to claim 7 wherein $R^5$ is ethoxycarbonyl, 1-hydroxy-1-methylethyl, acetyl, or hydroxymethyl.

9. Ethyl 3-methyl-8-(1-methylethyl)-2-(phenylmethyl)-2-azabicyclo[2.2.2]octane-6-carboxylate or an acid-addition salt thereof according to claim 8.

10. Ethyl 3,4,8-trimethyl-2-(phenylmethyl)-2-azabicyclo-[2.2.2]octane-6-carboxylate or an acid-addition salt thereof according to claim 8.

11. A pharmaceutical composition which comprises a compound of the formula:

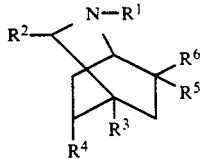

wherein:
$R^1$ is hydrogen, lower-alkyl Or phenyl-lower-alkyl;
$R^2$ is lower-alkyl or phenyl-lower alkyl;
$R^3$ is hydrogen or lower-alkyl;
$R^4$ is lower-alkylidene or lower-alkyl; or $R^3$ and $R^4$ together are —(CH$_2$)$_n$— wherein n is an integer from three to five;
$R^5$ is lower-alkoxycarbonyl, hydroxylower-alkyl, carboxy, or lower-alkanoyl; and
$R^6$ is hydrogen, lower-alkoxycarbonyl, hydroxylower-alkyl, lower-alkylthio, or lower-alkyl;
or a pharmaceutically acceptable acid-addition salt thereof; together with a pharmaceutically acceptable carrier, adjuvant, diluent or vehicle; with the proviso that when $R^6$ is lower-alkoxycarbonyl, $R^5$ must be lower-alkoxycarbonyl.

12. A pharmaceutical composition according to claim 11 wherein $R^1$ is hydrogen, methyl or phenylmethyl; $R^2$ is methyl or phenylmethyl; $R^3$ is hydrogen or methyl; and $R^4$ is ethylidene, methyl, ethyl or isopropyl; or $R^3$ and $R^4$ together are —(CH$_2$)$_4$—.

13. A pharmaceutical composition according to claim 12 wherein $R^5$ is ethoxycarbonyl, 1-hydroxy-1-methylethyl, acetyl, or hydroxymethyl; and $R^6$ is hydrogen, ethoxycarbonyl, methylthio or methyl.

14. A pharmaceutical composition according to claim 13 wherein the compound is selected from the group consisting of ethyl 3-methyl-8-(1-methylethyl)-2-(phenylmethyl)-2-azabicyclo-[2.2.2]octane-6-carboxylate and ethyl 3,4,8-trimethyl-2-(phenylmethyl)-2-azabicyclo[2.2.2]octane-6-carboxylate or an acid-addition salt thereof.

15. A method for the treatment of central nervous system disorders which comprises administering to a patient in need of such treatment an effective amount of a compound of the formula

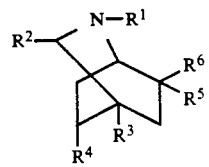

wherein:
$R^1$ is hydrogen, lower-alkyl or phenyl-lower-alkyl;
$R^2$ is lower-alkyl or phenyl-lower-alkyl;
$R^3$ is hydrogen or lower-alkyl;
$R^4$ is lower-alkylidene or lower-alkyl; or $R^3$ and $R^4$ together are —(CH$_2$)$_n$— wherein n is an integer from three to five;
$R^5$ is lower-alkoxycarbonyl, hydroxylower-alkyl, carboxy, or lower-alkanoyl; and
$R^6$ is hydrogen, lower-alkoxycarbonyl, hydroxylower-alkyl, lower-alkylthio, or lower-alkyl;
or a pharmaceutically acceptable acid-addition salt thereof; with the proviso that when $R^6$ is lower-alkoxycarbonyl, $R^5$ must be lower-alkoxycarbonyl.

16. A method according to claim 15 wherein said central nervous system disorder is a psychoses.

17. A method according to claim 16 wherein $R^1$ is hydrogen, methyl or phenylmethyl; $R^2$ is methyl or phenylmethyl; $R^3$ is hydrogen or methyl; and $R^4$ is ethylidene, methyl, ethyl or isopropyl; or $R^3$ and $R^4$ together are —(CH$_2$)$_4$—.

18. A method according to claim 17 wherein $R^5$ is ethoxycarbonyl, 1-hydroxy-1-methylethyl, acetyl, or hydroxymethyl; and $R^6$ is hydrogen, ethoxycarbonyl, methylthio or methyl.

19. A method according to claim 18 wherein the compound is selected from the group consisting of ethyl 3-methyl-8-(1-methylethyl)-2-(phenylmethyl)-2-azabicyclo[2.2.2]octane-6-carboxylate and ethyl 3,4,8-trimethyl-2-(phenylmethyl)-2-azabicyclo[2.2.2]octane-6-carboxylate or an acid-addition salt thereof.

* * * * *